(12) United States Patent
Podella et al.

(10) Patent No.: US 7,476,529 B2
(45) Date of Patent: Jan. 13, 2009

(54) ALTERING METABOLISM IN BIOLOGICAL PROCESSES

(75) Inventors: Carl W. Podella, Irvine, CA (US); Nils Siegfried Hauptmann, Orange, CA (US)

(73) Assignee: Advanced BioCatalytics Corporation, Irvine, CA (US)

( * ) Notice: Subject to any disclaimer, the term of this patent is extended or adjusted under 35 U.S.C. 154(b) by 282 days.

(21) Appl. No.: 10/799,529

(22) Filed: Mar. 11, 2004

(65) Prior Publication Data

US 2004/0180411 A1    Sep. 16, 2004

Related U.S. Application Data

(60) Provisional application No. 60/454,171, filed on Mar. 11, 2003, provisional application No. 60/454,178, filed on Mar. 11, 2003.

(51) Int. Cl.
*C12N 1/38* (2006.01)
*C12P 21/00* (2006.01)
*C12N 1/20* (2006.01)
*C12N 1/14* (2006.01)

(52) U.S. Cl. .................. 435/244; 435/71.1; 435/252.1; 435/255.1

(58) Field of Classification Search ........................ None
See application file for complete search history.

(56) References Cited

U.S. PATENT DOCUMENTS

| | | | |
|---|---|---|---|
| 2,320,479 A | 6/1943 | Sperti | |
| 3,404,068 A | 10/1968 | Battistoni | |
| 3,635,797 A | 1/1972 | Battistoni et al. | |
| 4,683,294 A * | 7/1987 | Van Wijnendaele et al. | 530/371 |
| 5,238,925 A | 8/1993 | Bentley | |
| 5,356,874 A | 10/1994 | Bentley | |
| 5,514,591 A | 5/1996 | Levin | |
| 5,714,169 A | 2/1998 | Levin | |
| 5,820,758 A | 10/1998 | Dale et al. | |
| 5,849,566 A | 12/1998 | Dale et al. | |
| 5,885,950 A | 3/1999 | Dale et al. | |
| 5,897,928 A | 4/1999 | Sanders et al. | |
| 6,033,875 A | 3/2000 | Bussineau et al. | |
| 6,100,072 A * | 8/2000 | Brucato et al. | 435/69.7 |
| 6,428,984 B1 * | 8/2002 | Pointek et al. | 435/69.3 |

OTHER PUBLICATIONS

"Baker's Yeast Production" (Chap. 6, pp. 261-313) Yeast Techn. 2nd Ed., AVI 1991.
William D. Pandolfe, Ph.D., "Cell Disruption by Homogenization" APV Homogenizer Group 1993.
Donna J. Schlemm, et al. "Medicinal Yeast Extracts" Cell Stress and Chaperones (Feb. 1999, 4 (3), pp. 171-176).
J. Peter Bentley, Ph.D., et al. "Peptides From Live Yeast Cell Derivative Stimulate Wound Healing" Arch Surg (May 1009, vol. 124, pp. 641-646) (1990).
Euan W. Low, et al. "Reducing Production of Excess Biomass During Wastewater Treatment" Wat. Res., (vol. 33, No. 5, pp. 1119-1132, 1999).
Euan W. Low, et al. "The Use of Chemical Uncouplers for Reducing Biomass Production During Biodegradation" Wat. Sci. Tech. (vol. 37, No. 4-5, pp. 399-402, 1998).
James B. Russell, et al. "Energetics of Bacterial Growth: Balance of Anabolic and Catabolic Reactions" Microbiological Reviews (Mar. 1995, pp. 48-62).

* cited by examiner

*Primary Examiner*—Nancy Vogel
(74) *Attorney, Agent, or Firm*—Sam K. Tahmassebi (57) ABSTRACT

Compositions of peptides and surface-active agents are described, as are methods of making and using such compositions. The compositions are capable of affecting metabolic rates in biological systems, and to accelerate nutrient uptake without a concomitant increase in biofilm production.

36 Claims, 1 Drawing Sheet

FIGURE 1

ALTERING METABOLISM IN BIOLOGICAL PROCESSES

This application claims priority from U.S. Provisional Application Ser. No. 60/454,171, filed Mar. 11, 2003, which application is hereby incorporated by reference in its entirety as if fully set forth herein. This application claims priority from U.S. Provisional Application Ser. No. 60/454,178, filed Mar. 11, 2003, which application is hereby incorporated by reference in its entirety as if fully set forth herein.

FIELD OF THE INVENTION

The present invention relates generally to compositions of surface-active agents combined with peptides derived from *Saccharomyces cerevisiae*, combinations of which are useful in altering metabolism in biological processes. The present invention further relates to methods of making and using compositions comprising surface-active agents in combination with peptides derived from *Saccharomyces cerevisiae*, particularly for use in treating wastewater.

BACKGROUND

There currently exist methods that can affect the rates by which biological metabolic processes proceed. The ability to alter these processes would find applications where reductions in biomass and biofilm production, accelerated nutrient uptake, improved fermentation rates, as well as methods for altering biochemical processes would be beneficial.

Acceleration of nutrient uptake without a concomitant increase of biomass can be achieved by uncoupling biochemical degradation (catabolism) from biochemical synthesis (anabolism). Uncoupling can occur during oxidative phosphorylation resulting in lower adenosine triphosphate (ATP) formation, or by dissipating generated ATP through "energy spilling". There are some chemical moieties known to uncouple oxidative phosphorylation, however they are inherently toxic and cost prohibitive.

Figure 1:
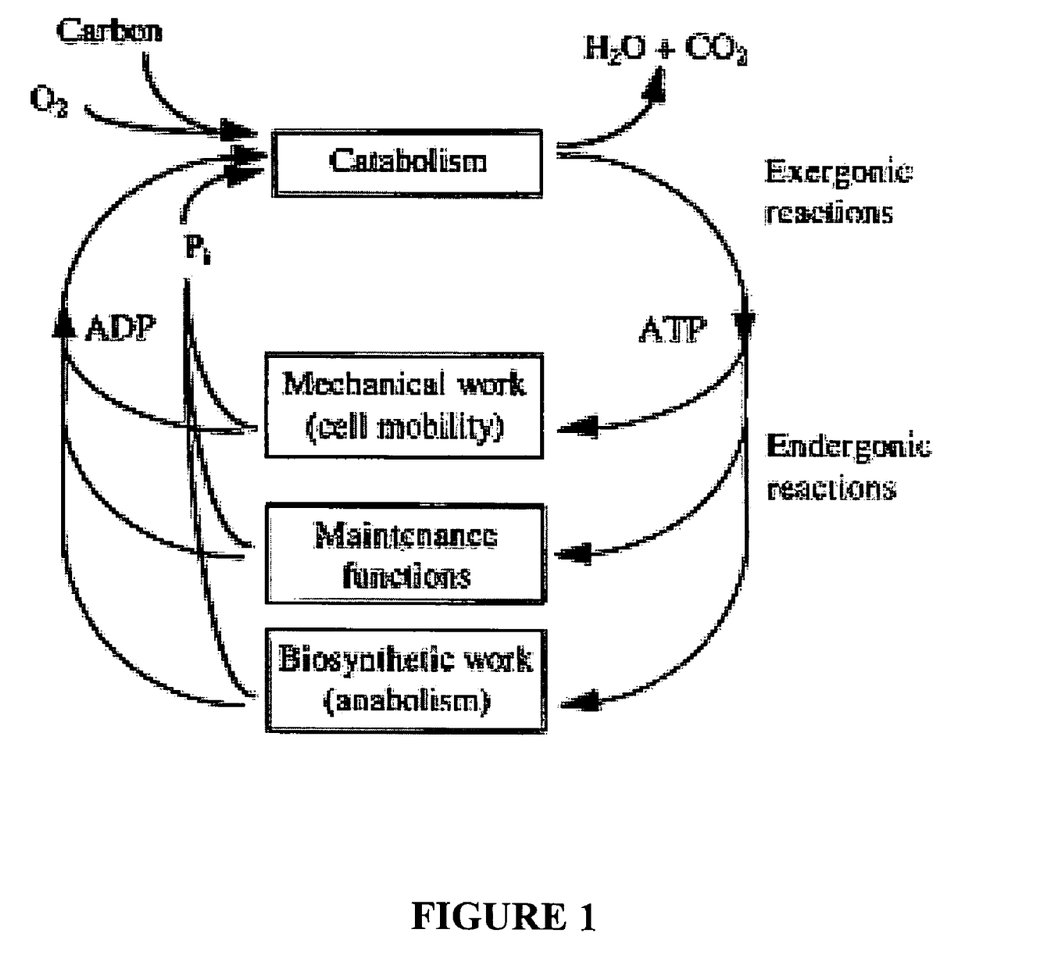
FIG. 1 is a graphic representation of the role of the ATP-ADP cycle in cell metabolism. (Adapted from B. Atkinson and F. Mavituna, Biochemical Engineering and Biotechnology Handbook, 2nd Edition, pp. 130-131, Stockton, N.Y. (1991)).

All microorganisms have the common purpose of using catabolism to conserve free energy by distributing it among compounds that can store and carry energy to where it is required in the cell. Intracellular regulation of catabolic and anabolic processes by bacteria is necessary to ensure an efficient flow of energy. Atkinson B. and Mavituna F., Biochemical Engineering and Biotechnology Handbook, 2nd Edition, pp. 130-131, Stockton, N.Y. (1991), describe the role of adenosine diphosphate-adenosine triphosphate (ADP-ATP) as follows: The high-energy phosphate bonds of ATP are used in coupled reactions for carrying out energy-required functions, wherein ultimately ADP and inorganic phosphate are formed. ADP is rephosphorylated to ATP during energy yielding reactions of catabolism. (See FIG. 1). Within the mitochondria of higher organisms, the concentration of ATP is known to regulate the activity in the citric acid cycle, in effect producing a feedback control loop. (Stryer, L., Biochemistry, 3rd Edition. Freeman, N.Y. (1988)).

Senez, J. C., Some Considerations on the Energetics of Bacterial Growth, Bacteriol. Rev. 26, 95-107 (1962), suggests that bacterial anabolism is coupled to catabolism of substrate through rate-limiting respiration. However, uncoupled metabolism would occur if respiratory control did not exist and instead, the biosynthetic processes were rate limiting. Therefore, the excess free energy would be directed away from the production of biomass.

Senez, in describing the link between energy-yielding reactions and the energy-consuming reaction of cell biosynthesis, conceptualized any anomaly as "uncoupling". Russell and Cook (Microbiological Reviews, March 1995, pp. 48-62) declared this all-inclusive definition did not differentiate between the production of ATP and the utilization of ATP in non-growth reactions. Because the latter process would be more aptly termed ATP energy spilling, therefore defining uncoupling as the inability of chemiosmonic mechanisms to generate the theoretical amount of metabolic energy in the form of ATP. This is redefined as "uncoupled oxidative phosphorylation" to differentiate it from other mechanisms.

Stouthamer, A. H., Correlation of Growth Yields In Microbial Biochemistry, International Review of Biochemistry, Ed. J. R. Quayle, Vol. 21, pp. 1-47, University Park, Baltimore (1979), reports that uncoupled metabolism has been observed in the presence of the following conditions: 1) in the presence of inhibitory compounds, 2) in the presence of excess energy source, 3) at unfavorable temperatures, 4) in minimal media, and 5) during transition periods in which cells are adjusting to changes in their environment.

Low and Chase (Wat. Res., Vol. 33, No. 5, pp. 1119-1132, 1999) theorize that decreasing the ATP available for biosynthesis would, in turn, reduce biomass production. The ability to replicate these uncoupling processes in wastewater treatment would be advantageous. Further, if microorganisms exhibit similar behavior to mitochondria in the regulation of the activity in the citric acid cycle, then a reduction of cellular ATP production would provide a stimulus to the feedback loop to promote accelerated catabolism of pollutants.

There exist several possibilities for the consumption or loss of energy required for biomass production, including the dissipation of energy as heat by adenosine triphosphate systems, the activation of alternative metabolic pathways bypassing free energy conserving reactions, and the accumulation of polymerized products in storage form or as secreted waste.

Protonophores are reagents that exhibit the ability to disrupt the tight coupling between electron transport and the ATP synthase of the respiratory chain, because they dissipate the proton gradient across the inner mitochondrial membrane created by the electron transport system. Typical examples include: 2,4-dinitrophenol, dicumarol, and carbonyl cyanide-p-trifluoromethoxyphenyl hydrazone. These compounds share two common features: hydrophobic character and a dissociable proton. As uncouplers, they function by carrying protons across their inner membrane. Their tendency is to acquire protons on the cytosolic surface of the membrane (where the proton concentration is high) and carry them to the matrix side, thereby destroying the proton gradient that couples electron transport and the ATP synthase. The energy released in electron transport is dissipated as heat. Biochemistry, 2nd Edition, Garrett and Grisham (1999)

Addition of protonphores to uncouple the energy generating mechanisms of oxidative phosphorylation will stimulate the specific substrate rate uptake while reducing the rate of biomass production.

Low and Chase (Wat. Sci. Tech., Vol. 37, No. 4-5, pp. 399-402, 1998) supplemented a chemostat monoculture of *P. putida* with the protonphoric uncoupler of oxidative phosphorylation, para-nitrophenol. The effect of this addition was to dissipate energy within the cells and thus reduce the energy available for endothermic processes. Under these conditions, cells continued to satisfy their maintenance energy requirements prior to making energy available for anabolism, thus reducing the observed biomass yield.

Through catabolism, cells make biologically useful energy available for fueling their endothermic reactions. An increase of the energy requirements for non-growth activities, in particular maintenance functions, would decrease the amount of energy available for biosynthesis of new biomass. Endothermic maintenance functions include the turnover of cell materials and osmotic work to maintain gradients. The net effect is a utilization of ATP through 'futile cycles' also called energy spilling, which reduces the amount of ATP available for the synthesis of biomass. Also, energy requirements for cell motility cannot be differentiated from maintenance energy requirements. (Low and Chase, 1998)

The discovery and use of peptides produced from *Saccharomyces cerevisiae* for medicinal applications described by George Sperti in U.S. Pat. Nos. 2,320,478, 2,320,479 and 2,239,345, illustrate a method for producing low molecular weight heat-shock proteins, referred to as Live Yeast Cell Derivative (LYCD), that has demonstrated the ability to affect skin respiration. The active peptides in the LYCD have been isolated and identified by a number of individuals. Bentley, U.S. Pat. No. 5,356,874 and Bentley et al. (Peptides From Live Yeast Cell Derivative Stimulate Wound Healing, Arch Surg, Vol. 125, pp. 641-46, May 1990) describe the active ingredients as an angiogenic factor comprising a mixture of polypeptides having molecular weights ranging between about 6,000 daltons to about 17,000 daltons, said factor isolated from a yeast cell derivative. Schlemm et al. (Medicinal Yeast Extracts, Cell Stress & Chaperones (1999) 4(3) 171-76) further defines these extracts as the 15,700 dalton yeast copper, zinc-superoxide dismutase, the 10,100 dalton acyl CoA binding protein (ACBP), the 8,560 dalton ubiquitin protein and the 7,090 dalton peptide of the C-terminal fragment of heat-shock protein 12, a glucose-lipid regulated protein.

Enzymatic compositions founded on yeast extracts have been used for the treatment of wastewater. Battistoni, U.S. Pat. No. 3,635,797, describes a multi-enzymatic composition comprised of an enzymatic fermentation reaction product, surfactants, citric and lactic acids, urea and pine oil. Battistoni claims the composition greatly improves sewage treatment facility capabilities by stimulating bacterial growth, eliminating odors, and enzymatically improving the catalytic degradation of sewage impurities. The Battistoni patent describes an anaerobic yeast fermentation process as follows:

"Approximately 1,000 gallons of warm softened water having a temperature of between about 85-100 degrees F. was placed in a large tank. To the water was added 700 pounds of black untreated cane molasses, 210 pounds raw cane sugar and 10 pounds magnesium sulfate. The mixture was thoroughly blended, after which 95 pounds diastatic malt and 10 pounds bakers yeast were added and agitated slightly. The composition was allowed to stand for about 3 days, after which the effervescent reaction had subsided, indicating essentially complete fermentation."

Because it is performed without active aeration or agitation, the fermentation process described in Battistoni is considered anaerobic in nature.

Dale, U.S. Pat. No. 5,879,928, describes a composition for the treatment of municipal and industrial wastewater, comprised of a yeast fermentation supernatant, preservatives and a non-ionic surfactant. The composition comprises a fermentation supernatant from a *Saccharomyces cerevisiae* culture, sodium benzoate, imidazolidinyl urea, diazoldinyl urea and a non-ionic surfactant. The Dale patent describes a composition having desirable properties associated with surfactant micro bubbles. Dale explains that the micro bubbles formed with the composition appear to increase the mass transfer of oxygen in liquids. Further, the micro bubbles are the result of aggregates of surfactant molecules with a loose molecular packing more favorable to gas mass transfer characteristics because a surface consisting of fewer molecules would be more gas permeable than a well-organized micelle containing gas. Dale further describes biologically derived catalysts in combination with the surfactants, both of which tend to be amphiphilic; that is, they have pronounced hydrophobic and hydrophilic properties. The non-ionic surfactants used in the Dale composition are said to be compatible with, and enhance enzymatic reactions. However, Dale also states the composition has catalytic activities that are more like the catalytic activities of functionalized surfactants than conventional enzyme systems.

The composition of the Dale patent is similar to that described in the Battistoni patent; that is, the fermentation process is anaerobic in nature, with an added step of the removal of the resulting yeast cells by centrifugation. The Dale fermentation process is described as follows:

"The yeast, *Saccharomyces cerevisiae*, is cultured in a medium comprising: a sugar source, such as sucrose from molasses, raw sugar, soy beans or mixtures thereof. A sugar concentration of about 10 to about 30%, by weight; malt, such as diastatic malt at a concentration of about 7 to about 12%, by weight; a salt, such as magnesium salts, and in particular magnesium sulfate, at a concentration of about 1 to about 3%, by weight, and yeast is added to the medium to a final concentration on about 1 to about 5%, by weight, is used. The mixture is incubated at about 26 degrees to about 42 degrees C. until the fermentation is completed, i.e. until the effervescence of the mixture has ceased, usually about 2 to about 5 days, depending on the fermentation temperature. At the end of the fermentation, the yeast fermentation composition is centrifuged to remove the "sludge" formed during the fermentation."

Consistent with the Battistoni patent, without the presence of active aeration or agitation, the fermentation process described in the Dale patent is considered anaerobic in nature. Carbon mass balance studies, conducted under controlled conditions, indicate the Battistoni composition increases the rate of carbon metabolism versus an untreated control. Likewise, carbon mass balance studies conducted with the Dale composition yielded an even greater increase in the rate of carbon metabolized versus Battistoni and the control. However, the rate of conversion of carbon metabolized to biomass carbon of either composition remained relatively consistent with the conversion rate of the untreated control. This would indicate the uncoupling of metabolism is not a function of either the Dale or Battistoni compositions. Nor are the low molecular weight peptides described in the present application produced as a result of the anaerobic fermentation of *Saccharomyces cerevisiae* as described in either of the Battistoni or Dale patents.

Production of excess biomass during biological treatment of wastewaters requires costly disposal. With environmental and legislative constraints limiting disposal options, considerable impetus exists for reducing the amount of biomass produced. (Low E. W. and Chase H. A., The Effect of Maintenance Energy Requirements on Biomass Production During Wastewater Treatment, Water Research, Vol. 33, Issue 3, pp. 847-853. (2000)). The activated sludge process employs a microbial population that will convert organic pollutants to cell mass and respiration products. Cell mass accumulates within the process and the excess biomass must therefore be disposed of. Although such treatment and disposal may already account for 60% of total plant operating costs, (Horan N. J., Biological Wastewater Treatment Systems, Wiley, Chichester (1990)), these costs are expected to rise with new European Community (EC) legislation and decreasing landfill availability. Sludge disposal in the United States has also come under increasing scrutiny and new legislation regulating sludge disposal is being enacted by government agencies at all levels. (Low and Chase, The Use of Chemical Uncouplers for Reducing Biomass Production During Biodegradation, Wat. Sci. Tech., Vol. 37, No. 4-5, pp. 399-402, 1998).

Dissipating energy intended for anabolism of cell mass without reducing the rate of removal of organics from aqueous waste provides a direct mechanism for reducing the yield of biomass. The chemiosmonic mechanism of oxidative phosphorylation (by which adenosine diphosphate (ADP) to energy-rich adenosine triphosphate (ATP) is produced during catabolism, (Mitchell, P., Chemiosmonic Coupling and Energy Transduction: A Logical Development of Biochemical Knowledge, Bioenergetics 3, 5-24 (1961)), can be uncoupled using protonphores and under these circumstances is dissipated. Oxidation of the substrate still occurs, but the phosphorylation of ADP to ATP is reduced, and consequently, there is less energy available for the formation of biomass. (Simon, E. W., Mechanisms of Dinitrophenol Toxicity, Biol. Rev. 28, 453-479 (1953)).

SUMMARY OF THE INVENTION

Investigation into the use of yeast fermentation by-products for the purpose of ascertaining the degree to which these compounds affect biochemical metabolic shifts have resulted in the discovery of a group of low molecular weight proteins that, when combined with surface-active agents, result in an increased rate of catabolism without a concomitant increase in biomass production. While these low molecular weight proteins can be produced by *Saccharomyces cerevisiae* during aerobic fermentation as practiced by those familiar in the art, their yield increases significantly if the yeast cells are placed under stress conditions during or near the end of the fermentation process. These stress conditions can occur during periods of very low food to mass concentrations, or as the result of heat shock or pH shock conditions as described in U.S. Pat. No. 6,033,875, Bussineau et al.

It has further been found that compositions of Live Yeast Cell Derivative—which is an alcoholic derivative from *Saccharomyces cerevisiae* produced by the methods set forth U.S. Pat. Nos. 2,239,345, 2,230,478 and 2,230,479—coupled with surface-active agents, produce effects that simulate uncoupling of biochemical metabolic pathways when added to mixed-culture aerobic processes. The crude Live Yeast Cell Derivative was further refined utilizing dialysis membranes as set forth in U.S. Pat. No. 5,356,874, Bentley, yielding polypeptides having the molecular weights ranging between 6,000 and 17,000 daltons as determined by SDS-page electrophoresis. (Bentley, et al., 1990).

These low molecular weight (6-17 kD) proteins, in combination with surface-active agents, were found to yield an increase in catabolism of organic matter without the proportional increase in biomass, and also to increase the amount of carbon dioxide respired. Studies demonstrated the use of either the low molecular weight proteins or the surface-active agents alone showed little effect on the catabolic or anabolic rates. A synergistic effect was observed when surface-active agents were combined with the low molecular weight proteins of the present invention.

Thus, it is an object of this invention to describe compositions, based on yeast-derived low molecular weight proteins and surface-active agents, which have the ability to alter biological metabolic processes in such a way as to simulate the uncoupling of biochemical pathways.

It is another object of this invention to describe methods by which the production of low molecular weight proteins from *Saccharomyces cerevisiae* may be enhanced.

It is a further object of this invention to utilize the described compositions and methods to affect the catabolic and anabolic biological processes during the treatment of municipal and industrial wastewater treatment processes for the purposes of accelerating the biological degradation of organic wastewater contaminants, reducing the production of activated sludge, reducing the amount of aeration required as a result of the accelerated catabolic processes, reduction of biofilm in cross-flow membrane filtration and cooling towers, and cleaning compositions in non-sterile environments.

It is yet another object of the invention to stabilize the compositions through the use of anti-microbial agents and pH adjustment to provide long-term stability to the compositions.

DETAILED DESCRIPTION OF THE PREFERRED EMBODIMENTS

In the specification, the following terms are defined as follows:

The "aerobic yeast fermentation process" is defined as the standard propagation conditions utilized in the production of commercially available baker's yeast as described in the chapter entitled "Baker's Yeast Production", in Nagodawithana T. W. and Reed G., Nutritional Requirements of Commercially Important Microorganisms, Esteekay Associates, Milwaukee, Wis., pp 90-112 (1998), and further described below.

"Live Yeast Cell Derivative (LYCD)" is defined as an alcoholic extract obtained from baker's yeast prepared as described below.

The "uncoupling factors" are defined as the biologically active polypeptide fraction obtained from LYCD. While the preferred method for obtaining LYCD is an alcoholic extract, and the peptides of the "uncoupling factors" are found in the LYCD, we show that these "uncoupling factors" need not be derived from an alcoholic extract, but can be generated from an aerobic fermentation, and preferably followed by a heat shock process and some form of cell disruption.

The "surface-active agents" are defined as non-ionic and anionic surfactants as described below.

The present inventors have isolated an uncoupling factor derived from LYCD of aerobic yeast fermentation processes which, when coupled with surface-active agents, simulates uncoupling oxidative phosphorylation or energy spilling in biochemical processes. This factor is comprised of polypeptide fractions ranging in molecular weights between about 6,000 and 17,000 daltons as indicated by results of polyacrylamide gel electrophoresis. The polypeptide uncoupling factor of the present invention, when utilized in isolation, appears to have little or no effect on biological metabolism. Likewise, the use of the surface-active agents of the present invention in isolation, does not lead to a significant change of the metabolic rate. There is a synergistic effect created through the combination of surface-active agents with the uncoupling factor derived from yeast, that affect a profound change of the metabolism by uncoupling biochemical pathways.

The uncoupling factor may be produced by an aerobic yeast fermentation process. Yeast fermentation processes are generally known to those of skill in the art, and are described, for example, in the chapter entitled "Baker's Yeast Production" in Nagodawithana T. W. and Reed G., Nutritional Requirements of Commercially Important Microorganisms, Esteekay Associates, Milwaukee, Wis., pp 90-112 (1998), which is hereby incorporated by reference. Briefly, the aerobic yeast fermentation process is conducted within a reactor having aeration and agitation mechanisms, such as aeration tubes and/or mechanical agitators. The starting materials (liquid growth medium, yeast, sugars, additives) are added to the fermentation reactor and the fermentation is conducted as a batch process.

After fermentation, the fermentation product may be subjected to additional procedures intended to increase the yield of uncoupling factor produced from the process. Several examples of post-fermentation procedures are described in more detail below. Other processes for increasing yield of uncoupling factor from the fermentation process may be recognized by those of ordinary skill in the art.

Although *saccharomyces cerevisiae* is a preferred starting material, several other yeast strains may be useful to produce yeast ferment materials used in the compositions described herein. Additional yeast strains that may be used instead of or in addition to *Saccharomyces cerevisiae* include *Kluyveromyces marxianus, Kluyveromyces lactis, Candida utilis* (*Torula* yeast), *Zygosaccharomyces, Pichia, Hansanula*, and others known to those skilled in the art.

The surface-active agents used in the compositions are preferably surfactants. Surfactants that are useful in the compositions described herein may be either nonionic, anionic, amphoteric or cationic, or a combination of any of the above, depending on the application. Suitable nonionic surfactants include alkanolamides, amine oxides, block polymers, ethoxylated primary and secondary alcohols, ethoxylated alkylphenols, ethoxylated fatty esters, sorbitan derivatives, glycerol esters, propoxylated and ethoxylated fatty acids, alcohols, and alkyl phenols, alkyl glucoside glycol esters, polymeric polysaccharides, sulfates and sulfonates of ethoxylated alkylphenols, and polymeric surfactants. Suitable anionic surfactants include ethoxylated amines and/or amides, sulfosuccinates and derivatives, sulfates of ethoxylated alcohols, sulfates of alcohols, sulfonates and sulfonic acid derivatives, phosphate esters, and polymeric surfactants. Suitable amphoteric surfactants include betaine derivatives. Suitable cationic surfactants include amine surfactants. Those skilled in the art will recognize that other and further surfactants are potentially useful in the compositions depending on the particular application. For example, a blend of non-ionic and anionic surfactants has been found to provide particularly good results.

Preferred anionic surfactants used in the composition include CalFoam™ ES 603, a sodium alcohol ether sulfate surfactant manufactured by Pilot Chemicals Co., and Steol™ CS 460, a sodium salt of an alkyl ether sulfate manufactured by Stepan Company. Preferred nonionic surfactants used in the enzyme/surfactant compound include Neodol™ 25-7 or Neodol™ 25-9, which are C12-Cl 5 linear primary alcohol ethoxylates manufactured by Shell Chemical Co., and Genapol™ 26 L-60, which is a C12-C16 natural linear alcohol ethoxylated to 60E C cloud point (approx. 7.3 mol), manufactured by Hoechst Celanese Corp. It should be understood that these surfactants and the surfactant classes described above are identified only as preferred materials and that this list is neither exclusive nor limiting of the composition.

Turning to the preferred embodiments, the compositions comprise an aerobic yeast fermentation supernatant combined with surface-active agents. In the preferred embodiment, *saccharomyces cerevisiae* is grown under aerobic conditions familiar to those skilled in the art, using a sugar, preferably molasses as the primary nutrient source. Additional nutrients may include, but are not limited to, diastatic malt, diammonium phosphate, magnesium sulfate, ammonium sulfate zinc sulfate, and ammonia. The yeast is preferably propagated under continuous aeration and agitation between 30 degrees to 35 degrees C. and at a pH of 4.0 to 6.0. The process takes between 10 and 25 hours and ends when the fermentation broth contains between 4 and 8% dry yeast solids, (alternative fermentation procedures may yield up to 15-16% yeast solids), which are then subjected to low food-to-mass stress conditions for 2 to 24 hours. Afterward, the yeast fermentation product is centrifuged to remove the cells and cell fragments, and the surface-active agents are added to the supernatant.

In an alternative embodiment, the yeast fermentation process is allowed to proceed until the desired level of yeast has been produced. Prior to centrifugation, the yeast in the fermentation product is subjected to heat-stress conditions by increasing the heat to between 40 and 60 degrees C., for 2 to 24 hours, followed by cooling to less than 25 degrees C. The yeast fermentation product is then centrifuged to remove the yeast cell debris and the supernatant is blended with surface-active agents.

In a further alternative embodiment, the fermentation process is allowed to proceed until the desired level of yeast has been produced. Prior to centrifugation, the yeast in the fermentation product is subjected to physical disruption of the yeast cell walls through the use of a French Press, ball mill, high-pressure homogenization, or other mechanical or chemical means familiar to those skilled in the art, to aid the release of intracellular, low molecular weight polypeptides. It is preferable to conduct the cell disruption process following a heat shock, pH shock, or autolysis stage. The fermentation product is then centrifuged to remove the yeast cell debris and blended with surface-active agents.

In a still further alternative embodiment, the fermentation process is allowed to proceed until the desired level of yeast has been produced. Following the fermentation process, the yeast cells are separated out by centrifugation. The yeast cells are then partially lysed by adding 2.5% to 10% of the surfactant used in the final product formulation to the separated yeast cell suspension (10%-20% solids). In order to diminish the protease activity in the yeast cells, 1 mM EDTA is added to the mixture. The cell suspension and surfactants are gently agitated at a temperature of about 25° to about 35° C. for approximately one hour to cause partial lysis of the yeast cells. Cell lysis leads to an increased release of intracellular small proteins. After the partial lysis, the partially lysed cell suspension is blended back into the ferment and cellular solids are again removed by centrifugation. The product is then blended with surface-active agents.

In a still further alternative embodiment, fresh live *Saccharomyces cerevisiae* is added to a jacketed reaction vessel containing methanol-denatured alcohol. The mixture is gently agitated and heated for two hours at 60 degrees C. The hot slurry is filtered and the filtrate is treated with charcoal and stirred for 1 hour at ambient temperature, and filtered. The alcohol is removed under vacuum and the filtrate is further concentrated to yield an aqueous solution containing the heat shock proteins. This LYCD composition is then blended with water and surface-active agents.

In a still further alternative embodiment, the LYCD is further refined so as to isolate the active uncoupling factors utilizing Anion Exchange Chromatography of the crude LYCD, followed by Molecular Sieve Chromatography. The refined LYCD is then blended with water and surface-active agents.

In a still further alternative embodiment, the surface-active agents of the compositions are comprised of non-ionic surfactants.

In a still further alternative embodiment, the surface-active agents of the compositions are comprised of a blend of non-ionic surfactants and anionic surfactants.

In a still further alternative embodiment, preservatives and stabilizers are added to the compositions and the pH is adjusted to between 3.8 and 4.8 to provide long-term stability to the composition.

In a still further alternative embodiment, the compositions are used in the treatment of municipal and industrial wastewater wherein degradation of biologically available wastewater contaminants is accelerated without a concomitant increase in the production of sludge.

The compositions prepared by the preceding processes are useful in a number of applications where bacteria, or yeast, are utilized in the application. For example, the compositions may be useful in applications having as a goal the destruction or removal of organic compounds, such as treating wastewater or other bioremediation. Alternatively, the compositions may be useful in applications having as a goal the creation of fermentation beer or antibiotics. Other types of applications for which the compositions may be useful are those in which biomass or biofilm production is sought to be minimized, which is achieved by the compositions described herein by the uncoupling of the ATP cycle and the effect on reproduction of bacteria and production of polysaccharides (biofilm). These applications are useful, for example, in the reduction of hydrogen sulfide in sewers where bacteria form biofilm, thus creating anaerobic conditions that are conducive to the production of hydrogen sulfide, or in the reduction of calcium carbonate in cooling towers where calcium salts peg onto biofilm and clog circulation systems, or in the minimization or elimination of biofilm in medical products. Specific applications include, but are not limited to, the following: municipal wastewater plants, industrial wastewater plants (particularly food processing), sewage lines, septic tanks and septic fields, cross-flow membrane filtration systems, cooling towers, soil remediation, bilgewater in ships, odor control applications, agricultural applications (e.g., cattle and chicken manure ponds), clarification of standing bodies of water in facultative lakes, ponds, and lagoons, pools/spas, cleaners for non-sterile environments, and the like. Although several examples are listed, the person of ordinary skill in the art will appreciate that the compositions described herein will have additional applications not explicitly set forth herein, but which are natural extensions of those listed and/or which are contemplated by the general mode of action of these compositions as described herein.

Test Method

The carbon mass balance studies described herein utilized a sterile nutrient broth solution using Bacto Tryptic Soy Broth, produced by Becton Dickinson and Company, that was inoculated with Polyseed, a proprietary blend of aerobic bacteria produced by InterLab, approved by the U.S. Environmental Protection Agency for Biological Oxygen Demand (BOD) determination. Tryptic Soy Broth was chosen as a nutrient because it is a defined Chemical Composition and is completely soluble. Hence, any suspended solids or particulate matter that develop during the course of the study is assumed to be biomass produced as a result of the assimilation of organic carbon. Since it is known that approximately 51% of a bacterial cell consists of carbon, one can determine the rate of carbon in the nutrient substrate that is converted to biomass by analyzing unfiltered versus filtered samples for total organic carbon at the beginning of the experiment, followed by sample analysis at any point in time during the study.

Carbon mass balance studies were conducted to determine the ability of the present invention to affect changes in carbon uptake, rate of conversion of carbon to biomass or to carbon dioxide, respectively. The studies were conducted utilizing a 2 liter reactor vessel, Applikon Bio Console, Model ADI 1025 and an Applikon BioController, Model ADI 1010 using air that had been sparged through a 1.5N sodium hydroxide solution followed by sparging through 2× deionized water to remove all carbon dioxide from the aeration source. The bioreactor exhaust air was then sparged through a 1.5N sodium hydroxide solution trap and the amount of carbon dioxide respired in the bioreactor during the test period was determined.

A Tryptic Soy Broth solution was prepared by adding 72 grams of sterile 10% Tryptic Soy Broth concentrate to 2400 ml of 2×-deionized water in a 4 l. beaker. Two capsules of Polyseed inoculum were added to the nutrient solution. The inoculated nutrient was warmed up and maintained at 30 degrees C., with continuous agitation using a stir bar for 14 hours. Prior to transferring the nutrient to the bioreactor, the nutrient solution was filtered through 4 layers of cheesecloth to remove the grain used as the substrate for the bacteria inoculum. Two liters of the nutrient solution were charged into the bioreactor. The "Treated" samples had 10 mg/l of the test composition (unless different dose levels are noted) added to the nutrient, while deionized water was added to the "Control" at the same 10 mg/l.

The bioreactor was then sealed and carbon dioxide-free air was sparged at a feed rate of 1.0 liter per minute while the bioreactor temperature was maintained at 30 degrees C. and the turbine mixer ran at 500 RPM for the duration of the test. The exhaust air was sparged through a 1.5 M sodium hydroxide solution to capture the carbon dioxide being respired.

Upon completion of the test, the sodium hydroxide solution was transferred to a beaker and 20 ml of a 3.5N barium chloride solution was added. The solution was neutralized with 4N hydrochloric acid using a pH meter and a buret to determine the volume of hydrochloric acid solution required to neutralize the solution. This is the value for B. The standardization factor was created by neutralizing 200 ml of 1.5N sodium hydroxide solution with 4N hydrochloric acid using a pH meter and a buret to determine the volume of hydrochloric acid solution required to neutralize the solution. This determined the value for S. The amount of carbon respired as carbon dioxide was then calculated using S and B in the following equation: $C=6N(B-S)$ where $N=7.5$ The nutrient was sampled at 0 hours and again at the conclusion of the study. Filtered and unfiltered nutrient samples were analyzed for total organic carbon (TOC) using a Shimadzu Total Organic Carbon Analyzer, Model TOC-5000A.

The Carbon Mass Balance is calculated as follows: Carbon Nutrient Consumed=Carbon Biomass Increase+Carbon Respired as Carbon Dioxide.

Determination of the level of biomass carbon was achieved by determining the difference between the total TOC and soluble TOC of any sample.

Evaluations of Compositions

The compositions described herein have utility in the treatment of municipal and industrial wastewater by accelerating the metabolism of biologically available nutrients without producing a concomitant increase biomass. This feature creates opportunities for the operators of these facilities to achieve greater wastewater throughput, relieve overcapacity conditions, and reduce the expense required for sludge disposal. Tables 2, 4, 6, 8, 10, 12, 14 and 15 demonstrate the ability of the compositions to achieve these benefits.

EXAMPLE 1

*Saccharomyces cerevisiae* was cultivated under aerobic conditions familiar to those skilled in the art, using molasses as the primary nutrient source. Additional nutrients can include diastatic malt, diammonium phosphate, magnesium sulfate, ammonium sulfate zinc sulfate, and ammonia. The yeast was propagated under continuous aeration and agitation between 30 degrees and 35 degrees C. and a pH range of between 4.0 and 6.0 until the yeast attained a minimum level of 4% based on dry weight and the yeast was then subjected to low food-to-mass stress conditions for a period of 4 hours. At the conclusion of the fermentation process, the yeast fermentation product was centrifuged to remove the yeast cells and the supernatant was then blended with surface-active agents and the pH adjusted between 3.8 and 4.8 for stability.

EXAMPLE 2

*Saccharomyces cerevisiae* was cultivated utilizing the conditions found in Example 1. At the conclusion of the fermentation process, the fermentation product was heated to 50 degrees C. for eight hours so as to induce the heat shock response and perform autolysis on the yeast cells, thus releasing the heat-shock proteins into the growth media. At the conclusion of the autolysis process, the yeast fermentation product was centrifuged to remove the yeast cells and the supernatant was then blended with surface-active agents and the pH adjusted between 3.8 and 4.8 for stability.

EXAMPLE 3

*Saccharomyces cerevisiae* was cultivated utilizing the conditions found in Example 1. At the conclusion of the fermentation process, the fermentation product was heated to 40 degrees C. for two hours so as to induce the heat shock response and perform autolysis on the yeast cells, thus releasing the heat-shock proteins into the growth media. At the conclusion of the autolysis process, the fermentation product was passed through a Manton-Gaulin High Pressure Homogenizer at 7000 psi for three cycles, after which the yeast fermentation product was centrifuged to remove the yeast cell debris and the supernatant was then blended with surface-active agents and the pH adjusted between 4.0 and 4.6 for stability. Formulae for the three examples are as follows:

TABLE 1

| Material | % By Weight | | |
|---|---|---|---|
| | Example 1 | Example 2 | Example 3 |
| Non-autolysed Ferment | 64.50% | | |
| Autolysed Ferment | | 64.50% | |
| Disrupted Cell Ferment | | | 64.50% |

TABLE 1-continued

| Material | % By Weight | | |
|---|---|---|---|
| | Example 1 | Example 2 | Example 3 |
| Ethoxylated Linear Alcohol - 7 mole ETO | 26.60% | 26.60% | 26.60% |
| Alkyl Ether Sulfate, Sodium | 8.90% | 8.90% | 8.90% |
| Salt (60%) | | | |
| Adjust pH to 4.0 with Phosphoric Acid | | | |
| Total | 100.00% | 100.00% | 100.00% |

As shown in Table 2, results of the carbon mass balance bench test using Examples 1-3 at 10 mg/l versus an untreated control indicate an increase in carbon uptake of between 100-160% when compared to the control, without a concomitant increase in biomass. Respiration rates exhibited a 4 to 5 fold increase for the treated samples. Results were as follows:

TABLE 2

Carbon Mass Balance Comparisons of Modified Aerobic Fermentations Processes vs.: Control

| | Control | Example 1 | Example 2 | Example 3 |
|---|---|---|---|---|
| Nutrient TOC/mg/l | | | | |
| 0 Hour | 891.2 | 924.3 | 863.6 | 854.0 |
| 4 Hours | 715.9 | 571.3 | 509.1 | 398.1 |
| ΔTOC | 175.3 | 353.0 | 430.0 | 455.9 |
| Biomass TOC/mg/l | | | | |
| 0 Hour | 81.2 | 65.9 | 39.2 | 71.7 |
| 4 Hours | 224.0 | 213.1 | 277.5 | 321.9 |
| ΔTOC 1 | 142.8 | 147.2 | 238.3 | 250.2 |
| Nutrient TOC to Biomass TOC % | 81.5 | 41.7 | 55.5 | 55.3 |
| Carbon Dioxide as Carbon mg/l | 49.5 | 198.0 | 220.5 | 252.0 |

EXAMPLE 4

Composition is based on U.S. Pat. No. 3,635,797 wherein the fermentation process was conducted under anaerobic conditions; that is, no active aeration was applied to the fermentation vessel during the fermentation process, and no agitation was utilized. The ferment was allowed to stand for about 3 days, after which the effervescent reaction had subsided.

EXAMPLE 5

Composition is based on U.S. Pat. No. 5,879,928 wherein the fermentation process was conducted under anaerobic conditions wherein the fermentation mixture is incubated at about 26 degrees to about 42 degrees C. until the fermentation is completed, i.e. until effervescence of the mixture has ceased, usually about 2 to about 5 days, depending on the fermentation temperature. At the end of the fermentation, the yeast fermentation composition is centrifuged to remove the "sludge" formed during the fermentation.

TABLE 3

|  | % By Weight | |
| --- | --- | --- |
| Material | Example 4 | Example 5 |
| Fermentation Supernatant | 24.96% | 20.00% |
| Water | 61.76% | 70.54% |
| Nonionic Surfactants | 1.89% | |
| Anionic Surfactants | 4.53% | 9.00% |
| Inorganic Salts | 1.20% | |
| Lactic Acid | 0.93% | |
| Citric Acid | 0.17% | |
| Urea | 4.20% | |
| Pine Oil | 0.36% | |
| Sodium Benzoate | | 0.30% |
| Imidazolidinyl Urea | | 0.01% |
| Diazolidinyl Urea | 0.15% | |
| Total | 100.00% | 100.00% |

Results of the carbon mass balance studies compare the fermentation product differences between anaerobic processes of the prior art and the aerobic process of the present invention. Example 4, utilizing the teachings of U.S. Pat. No. 3,635,797 and treated with the composition at a dose rate of 30 mg/liter, affected a 40.2% increase in nutrient carbon uptake during the 4 hour duration of the study, and also a 38.4% increase in biomass production. However, the rate of nutrient carbon converted to biomass carbon remained virtually identical, 80.4% conversion for the Battistoni composition vs. 81.5% for the control.

Example 5, utilizing the teachings of U.S. Pat. No. 5,879,928 and also treatment level of the composition of 30 mg/liter, affected a 107.8% increase in carbon uptake vs. the control and 48.3% increase vs. the Battistoni composition, but also 135.4% and 128.4% increased in biomass production vs. the control and Battistoni composition, respectively. The amount of nutrient carbon being converted to biomass carbon increased over that of the control and Example 4 to a 92.3% carbon conversion rate.

Example 1, utilizing an aerobic fermentation procedure with a treatment level of 10 mg/liter, experienced a significant reduction in the conversion of nutrient carbon to biomass carbon, exhibiting at 48.8% reduction in biomass production relative to the amount of carbon metabolized. Moreover, the overall metabolism of nutrient carbon was essentially equivalent (3.2% decline) compared to the Dale composition and superior to that of Battistoni (43.7% increase) and the control (101.4% increase).

Examination of the protein concentrations of the products produced in the foregoing examples revealed the following:

Example 1 protein concentration: 33.38 mg/ml
Example 4 protein concentration: 13.88 mg/ml
Example 5 protein concentration: 3.01 mg/ml Thus, the anaerobic processes described in the Battistoni (U.S. Pat. No. 3,635,797) and Dale (U.S. Pat. No. 5,879,928) patents produced fermentation products having a significantly lower protein concentration than the fermentation products produced by the aerobic processes described herein.

Examination of the amount of nutrient carbon converted to biomass carbon, as well as the rates of carbon metabolism for the above examples, demonstrate the presence of an uncoupling factor when an aerobic fermentation process is implemented vis-à-vis the anaerobic processes described in the prior art. Whereas the compositions of the present invention exhibited a significant increase in the metabolism of the nutrient without a concomitant increase in biomass, compositions of the prior art demonstrated an ability to accelerate nutrient uptake, however the increase of biomass production was commensurate with the amount of nutrient assimilated. Results of this study were as follows:

TABLE 4

Carbon Mass Balance Comparisons of Fermentation Intermediates of U.S. Pat. No. 3,635,797, U.S. Pat. No. 5,879,928 and Example 1 vs. Control

|  | Control | Example 1 | Example 4 | Example 5 |
| --- | --- | --- | --- | --- |
| Nutrient TOC/mg/l | | | | |
| 0 Hour | 891.2 | 924.3 | 897.6 | 873.4 |
| 4 Hours | 715.9 | 571.3 | 651.9 | 509.1 |
| ΔTOC | 175.3 | 353.0 | 245.7 | 364.3 |
| Biomass TOC/mg/l | | | | |
| 0 Hour | 81.2 | 65.9 | 48.1 | 70.8 |
| 4 Hours | 224.0 | 213.1 | 245.7 | 407.0 |
| ΔTOC | 142.8 | 147.2 | 197.6 | 336.2 |
| % Nutrient TOC to Biomass TOC | 81.5 | 41.7 | 80.4 | 92.3 |
| CO2 as Carbon mg/l | 49.5 | 198.0 | 144.0 | 144.0 |

EXAMPLE 6

The formula was prepared in the same manner as shown in Example 3, except the surfactants were replaced by water to demonstrate the preference for inclusion of surface-active agents.

EXAMPLE 7

The formula was prepared using the surfactant combination utilized in Example 3 with water replacing the ferment so as to demonstrate the minimal effect of surface-active agents on the biological metabolic processes.

TABLE 5

|  | % By Weight | |
| --- | --- | --- |
| Material | Example 6 | Example 7 |
| Autolysed Ferment | 64.50% | |
| Water | 35.50% | 64.50% |
| Ethoxylated Linear Alcohol - 7 mole ETO | | 26.60% |
| Alkyl Ether Sulfate, Sodium Salt (60%) | | 8.90% |
| Adjust pH to 4.0 with Phosphoric Acid | | |
| Total | 100.00% | 100.00% |

Results of the mass balance bench tests shown in Table 6 indicate no significant shift in carbon uptake when applying fermentation product alone as in Example 6 at 10 mg/l or with surface-active agents as in Example 7 at 10 mg/l when compared to the untreated control. Results were as follows:

TABLE 6

Carbon Uptake Comparisons of Modified Aerobic Fermentations Processes -With and Without Surfactants, Surfactants Without Fermentation Product vs. Control

| Nutrient TOC/mg/l | Control | Example 1 | Example 6 | Example 7 |
|---|---|---|---|---|
| 0 Hour | 894.1 | 924.3 | 910.7 | 901.3 |
| 4 Hours | 705.0 | 571.3 | 729.9 | 737.5 |
| ΔTOC | 189.1 | 353.0 | 180.8 | 163.8 |
| Reduction: | 21.2% | 38.2% | 19.9% | 18.2% |

Utilization of nonionic and anionic surfactants at varying concentration, and their relationship to ferment at varying concentrations, impact the rate at which catabolism proceeds. A protocol was developed to determine these differences utilizing Tryptic Soy Broth at 3000 mg/liter as a carbon source, inoculated with aerobic bacteria, and incubated for 14 hours. The inoculated nutrient was stirred to ensure equal distribution of bacteria, and divided into 1 liter graduated cylinders. One cylinder was not treated for a control and the remaining cylinders were treated with compositions from Examples 8-13 at a dose level of 30 mg/L. All Examples utilized Disrupted Cell Ferment.

EXAMPLE 8

A combination of nonionic and anionic surfactants were utilized at a total active level of 9%, a disrupted cell ferment level of 20%, with water making up the balance of the composition.

EXAMPLE 9

Composition replicated Example 8, except the total surfactant level was reduced by 50%, however the ratio of nonionic to anionic surfactants was retained.

EXAMPLE 10

Composition replicated Example 9, except the level of disrupted cell ferment was increased by 50% and the water concentration was reduced by 10%.

EXAMPLE 11

Composition replicated Example 8, except the anionic surfactant was replaced by water in the composition.

EXAMPLE 12

Composition replicated Example 8, except the nonionic surfactant was replaced by water in the composition.

EXAMPLE 13

Composition replicated Example 10, except both anionic and nonionic surfactants were replaced with water in the composition.

Abbreviations:

| | |
|---|---|
| ELA | Ethoxylated Linear Alcohol - 7 mole ETO |
| AES | Alkyl Ether Sulfate, Sodium Salt (60%) |
| WAT | Water |
| DCF | Disrupted Cell Ferment |

TABLE 7

| | % By Weight | | | | | |
|---|---|---|---|---|---|---|
| Material | EX. 8 | EX. 9 | EX. 10 | EX. 11 | EX. 12 | EX. 13 |
| DCF | 20.00% | 20.00% | 30.00% | 20.00% | 20.00% | 30.00% |
| ELA | 7.50% | 3.75% | 3.75% | 7.50% | | |
| AES | 2.50% | 1.25% | 1.25% | | 2.50% | |
| WAT | 70.00% | 75.00% | 65.00% | 72.50% | 77.50% | 70.00% |
| Adjust pH to 4.0 with Phosphoric Acid | | | | | | |
| TOTAL | 100.00% | 100.00% | 100.00% | 100.00% | 100.00% | 100.00% |

Results demonstrated the interaction of the anionic surfactant when coupled with a nonionic surfactant and the disrupted cell ferment. Reducing the surfactant combination in Example 9 by 50% of the level utilized in Example 8 exhibited an 8% reduction in nutrient being metabolized. Increasing the ferment portion of the composition by 50% in Example 10, while maintaining the reduced surfactant level, resulted in a 20% increase in carbon metabolized when compared to Examples 8 and 9. Example 11, which contained only the nonionic surfactant and disrupted cell ferment product exhibited an 18% increase in efficacy, versus Exhibit 12, containing only the anionic surfactant with the ferment showed a slight decline. When the disrupted cell ferment was utilized at the same level as utilized in Exhibit 10, without benefit of any surfactant, a 75% decline in efficacy resulted for Example 13 versus the Exhibit 10 composition, and a 35% reduction when compared to the untreated control. Results were as follows:

TABLE 8

Relationships Between Nonionic Surfactants, Anionic
Surfactants and Disrupted Cell Fermentation Product
Compositions and Their Effects on Metabolic Rates

| Time | \multicolumn{7}{c}{Nutrient TOC = mg/L} | | | | | | |
|---|---|---|---|---|---|---|---|
| | Cont | Ex. 8 | Ex. 9 | Ex. 10 | Ex. 11 | Ex. 12 | Ex. 13 |
| Hour | | | | | | | |
| 0 | 920.0 | 920.0 | 920.0 | 920.0 | 920.0 | 920.0 | 920.0 |
| 2 | 859.3 | 697.4 | 758.1 | 597.1 | 533.6 | 747.0 | 857.4 |
| 4 | 782.0 | 560.3 | 644.9 | 469.2 | 458.2 | 579.6 | 826.2 |
| 6 | 728.6 | 511.5 | 543.7 | 427.8 | 437.0 | 528.1 | 796.7 |
| ΔTOC | 191.4 | 408.5 | 376.3 | 492.2 | 467.0 | 391.9 | 123.3 |
| Reduction: | 20.8% | 44.4% | 40.9% | 53.5% | 52.5% | 42.6% | 13.4% |

EXAMPLE 14

Composition replicated Example 11 except disrupted cell ferment was filtered through a 30 kD molecular weight cutoff centrifuge tube to remove all proteins larger that 30 kD to demonstrate the functionality of the low molecular weight peptides present in the disrupted cell ferment.

EXAMPLE 15

Composition replicated Example 14 except disrupted cell ferment was filtered through a 10 kD molecular weight cutoff centrifuge tube to remove all proteins larger that 10 kD to demonstrate the functionality of the low molecular weight peptides present in the disrupted cell ferment.

TABLE 9

| | % By Weight | |
|---|---|---|
| Material | Example 14 | Example 15 |
| D.C. Ferment <30 kD | 20.0% | |
| D.C. Ferment <10 kD | | 20.0% |
| Water | 72.5% | 72.5% |
| Ethoxylated Linear Alcohol - | 7.5% | 7.5% |
| 7 mole ETO | | |
| Adjust pH to 4.0 with | | |
| Phosphoric Acid | | |
| TOTAL | 100.00% | 100.00% |

Results showed no functional loss of metabolic efficiency due to removal of fermention-produced compounds of greater that 30 kD molecular weight, or compounds greater than 10 kD in the disrupted cell fermentation product. Data infers there may be some larger molecular weight (>10 kD) compound(s) that may contribute an inhibitory effect, thereby reducing some degree of biological metabolic efficiency of the uncoupling factor of the present invention. Results were as follows:

TABLE 10

Efficacy of Low Molecular Weight Peptides
Contained in Disrupted Cell Fermentation Product

| | \multicolumn{4}{c}{Nutrient TOC - mg/L} | | | |
|---|---|---|---|---|
| Time | Control | Example 11 | Example 14 | Example 15 |
| Hour | | | | |
| 0 | 863.0 | 866.9 | 865.7 | 861.4 |
| 2 | 779.1 | 779.4 | 761.1 | 794.7 |
| 4 | 691.4 | 677.8 | 605.9 | 705.1 |
| 6 | 608.8 | 554.7 | 495.7 | 604.5 |
| 8 | 499.7 | 401.9 | 279.4 | 268.5 |
| ΔTOC | 363.3 | 465.0 | 586.3 | 592.9 |
| Reduction: | 42.1% | 53.6% | 67.7% | 68.8% |

EXAMPLE 16

The composition and process were identical to that of Example 1, except refined LYCD utilizing dialysis membranes as set forth in U.S. Pat. No. 5,356,874, yielding polypeptides having the molecular weights ranging between 6,000 and 17,000 daltons was introduced into the formula at a level of 0.30%.

EXAMPLE 17

The composition and process are identical to that of Example 16, except refined LYCD utilizing dialysis membranes as set forth in U.S. Pat. No. 5,356,874, yielding polypeptides having the molecular weights ranging between 6,000 and 17,000 daltons replaced the fermentation product in the formula at a level of 1.00%. Formulae for the two examples are as follows:

TABLE 11

| | % By Weight | |
|---|---|---|
| Material | Example 16 | Example 17 |
| Non-autolysed Ferment | 64.20% | |
| Refined LYCD | 0.30% | 1.00% |
| Water | | 63.50% |
| Ethoxylated Linear Alcohol - | 26.60% | 26.60% |
| 7 mole ETO | | |
| Alkyl Ether Sulfate, Sodium | 8.90% | 8.90% |

TABLE 11-continued

| | % By Weight | |
|---|---|---|
| Material | Example 16 | Example 17 |
| Salt (60%) | | |
| Adjust pH to 4.0 with | | |
| Phosphoric Acid | | |
| Total | 100.00% | 100.00% |

Results of the carbon mass balance test using Examples 1, 16 and 17 at 10 mg/l versus a negative control demonstrated that the addition of 0.30% refined LYCD to the formula shown in Example 1, increased the uptake of carbon by 71% versus Example 1 formulation, and a carbon uptake increase of 230% when compared to the control. Respiration of carbon dioxide also increased by 83% versus the formula shown in Example 1, and a seven-fold increase when compared to the control. When the fermentation product was completely replaced by 1.00% refined LYCD in Example 17, an 84% increase of carbon dioxide was observed when compared to Example 1. Results were as follows:

TABLE 12

Carbon Mass Balance Comparisons of Modified
Aerobic Fermentation Process Composition vs. Control

| | Control | Example 1 | Example 16 | Example 17 |
|---|---|---|---|---|
| Nutrient TOC/mg/l | | | | |
| 0 Hour | 891.2 | 901.3 | 889.5 | 899.1 |
| 4 Hours | 715.9 | 577.9 | 337.4 | 321.2 |
| ΔTOC | 175.3 | 323.4 | 552.1 | 577.9 |
| Biomass TOC/mg/l | | | | |
| 0 Hour | 81.2 | 53.3 | 76.9 | 96.9 |
| 4 Hours | 224.0 | 195.4 | 360.4 | 401.0 |
| ΔTOC | 142.8 | 142.1 | 283.5 | 304.1 |
| Nutrient TOC to Biomass TOC % | 81.5 | 43.9 | 51.3 | 52.6 |
| CO2 as Carbon mg/l | 49.5 | 189.0 | 346.5 | 348.5 |

The relative increase of biomass production for Examples 16 and 17 was minor when compared to the significant increase of carbon uptake versus Example 1 and the Control. Additionally, the increase in biomass for Examples 16 and 17 was, in fact, directly proportional the increase of CO2 production. Therefore, the shift in the percent of nutrient TOC to biomass TOC (43.9% for Example 1 versus 51.3% for Example 16 and 52.6% for Example 17) may have reflected the margin of error inherent in conducting mass balance studies as opposed to determining theoretical results. An additional theory for the apparent upward shift in biomass production centers on the overabundance of assimilated carbon that resulted in sufficient production of energy so as to begin to overcome the uncoupling effect, thereby producing a slight increase in biomass production. Irrespective of the rationale for the shift observed, the use of refined LYCD, in conjunction with surface-active agents, resulted in an uncoupling of biochemical pathways yielding in a significant increase of carbon being metabolized and carbon dioxide respired, without the expected concomitant increase of biomass production.

EXAMPLE 18

This formulation replicates Example 3 except the fermentation product was passed through a 10,000 dalton molecular weight cutoff centrifuge tube to demonstrate the active proteins are of low molecular weight size.

EXAMPLE 19

This formulation is designed to demonstrate that the observed metabolic activity is not primarily a function of active enzymes. In the example, fermentation product was heated to 70 degrees C. for 24 hours, subsequently passed through a 10,000 dalton molecular weight cutoff centrifuge tube. Formulae for the two examples were as follows:

TABLE 13

| | % By Weight | | |
|---|---|---|---|
| Material | Example 3 | Example 18 | Example 19 |
| Disrupted Cell Ferment | 64.50% | | |
| Disrupted Cell Ferment <10 kD | | 64.50% | |
| Heated Disrupted Cell Ferment <10 kD | | | 64.50% |
| Ethoxylated Linear Alcohol - 7 mole ETO | 26.60% | 26.60% | 26.60% |
| Alkyl Ether Sulfate, Sodium | 8.90% | 8.90% | 8.90% |
| Salt (60%) | | | |
| Adjust pH to 4.0 with | | | |
| Phosphoric Acid | | | |
| Total | 100.00% | 100.00% | 100.00% |

Results of the Mass Balance Bench Test using Examples 3, 18 and 19 at a dose rate of 10 mg/l demonstrated a 22% decrease in the carbon uptake for Example 18 relative to Example 3 when the protein fractions above 10,000 daltons were removed from the fermentation product. The increase of carbon uptake, however, was still substantially higher compared to the control (by 103%). Further, the amount of biomass formed with Example 18 was 20% lower, keeping the ratio of nutrient consumed to biomass produced essentially the same as in Example 3. Heating of the disrupted cell fermentation product prior to removal of the protein fractions greater than 10,000 daltons had little effect on the carbon mass balance. Test results were as follows:

TABLE 14

Mass Balance Comparisons of Modified Aerobic
Fermentation Process Compositions and Yeast-
Derived Low Molecular Weight Proteins vs. Control

| | Control | Example 3 | Example 18 | Example 19 |
|---|---|---|---|---|
| Nutrient TOC/mg/l | | | | |
| 0 Hour | 891.2 | 854.0 | 922.8 | 899.8 |
| 4 Hours | 715.9 | 398.1 | 566.1 | 552.8 |
| ΔTOC | 175.3 | 455.9 | 356.7 | 347.0 |
| Biomass TOC/mg/l | | | | |
| 0 Hour | 81.2 | 71.7 | 71.0 | 36.3 |
| 4 Hours | 224.0 | 321.9 | 271.6 | 220.5 |
| ΔTOC | 142.8 | 250.2 | 200.6 | 184.2 |
| % Nutrient TOC to Biomass TOC % | 81.5 | 54.9 | 56.2 | 53.1 |
| Carbon Dioxide as Carbon mg/l | 49.5 | 252.0 | 211.5 | 157.5 |

A feature of the present invention is the ability to reduce the amount of aeration required in aerobic wastewater processes, which would result in energy savings; normally a substantial expense for wastewater treatment. This feature is possible with the present invention due to increased metabolism of BOD. In the early stages of the process, oxygen demand is greater for the treated test cylinder versus the control. Since a greater uptake of BOD is realized earlier in the process, the respiration of bacteria will decline in the absence of available or sufficient biologically available nutrient. Therefore, the oxygen demand decreases sooner for the treated test cylinder, thus resulting in a surplus of oxygen at the conclusion of the test period. This would permit a reduction in the total amount of aeration applied to the process. Results of that study were as follows:

TABLE 15

Relationship of Carbon Metabolism, Dissolved Oxygen and pH for Example 3 and Control

| Time | Nutrient TOC-mg/L | | pH | | Dissolved Oxygen-mg/L | |
|---|---|---|---|---|---|---|
| Hour | Control | Example 3 | Control | Example 3 | Control | Example 3 |
| 0 | 980.5 | 980.5 | 5.94 | 5.94 | 0.43 | 0.43 |
| 2 | 924.3 | 908.0 | 5.97 | 6.06 | 1.16 | 2.98 |
| 4 | 937.6 | 855.4 | 6.31 | 6.49 | 0.15 | 0.14 |
| 6 | 792.8 | 638.6 | 6.35 | 6.85 | 0.16 | 0.14 |
| 8 | 743.0 | 424.8 | 6.44 | 7.35 | 0.22 | 0.14 |
| 10 | 581.6 | 447.0 | 6.86 | 7.27 | 0.21 | 3.84 |
| 12 | 502.4 | 451.4 | 7.42 | 7.69 | 0.18 | 5.71 |
| 14 | 451.4 | 482.5 | 7.16 | 7.44 | 0.11 | 4.36 |
| 16 | 465.5 | 404.8 | 7.73 | 7.43 | 0.26 | 5.93 |

Results shown in Table 15 demonstrate the relationship between the level of bio-available nutrient (BOD) and the level of unutilized dissolved oxygen under comparable fixed, environmental and operating conditions for control and treated samples. The D.O of the treated sample increased after 8 hours dwell time when the bio-available nutrient declined, in this exhibit, below 450 mg/l of carbon. The D.O. of the control sample remained below 0.3 mg/l after 16 hours since the organic carbon level remained above 450 mg/l.

EXAMPLE 20

The aerobic fermentation process is not conducted under sterile conditions. Therefore, significant levels of bacterial contamination exist at the conclusion of the fermentation process. The presence of this contamination can facilitate a rapid degradation of the active peptides and surface-active agents, thereby rendering the composition less effective for its intended application. Therefore, the use of a broad-spectrum antimicrobial system is deemed useful. This example, based on the composition used in Example 3, illustrates a stabilization system that provides antimicrobial activity against a broad spectrum of organisms produced during the yeast fermentation process. The composition contains about 3 times the level required to adequately preserve the composition, thus providing a composition capable of being diluted with about 2 parts of water.

EXAMPLE 21

The treatment of large municipal wastewater treatment facilities is accomplished by utilizing a treatment level of about 1 to about 3 mg/l of Example 20. However, treatment of small wastewater flows can be difficult to accurately meter at this low dose rate. Therefore, it is desirable to provide a more dilute version of Example 20 wherein the stabilizer/preservative system is present at sufficient levels so as to prevent premature degradation of the composition. Example 21 is prepared with 35.5% of the active components used in Example 20 and the balance of the composition is comprised of water.

TABLE 16

| | % By Weight | | |
|---|---|---|---|
| Material | Example 3 | Example 20 | Example 21 |
| Disrupted Cell Ferment | 64.50% | 54.60% | 19.38% |
| Ethoxylated Linear Alcohol - 7 mole ETO | 26.60% | 22.50% | 7.50% |
| Alkyl Ether Sulfate, Sodium | 8.90% | 7.50% | 2.50% |
| Salt (60%) | | | |
| Propylene Glycol | | 14.60% | 5.18% |
| Sodium Benzoate | | 0.35% | 0.10% |
| Methyl Paraben | | 0.35% | 0.10% |
| Propyl Paraben | | 0.10% | 0.03% |
| Water | | | 65.21% |
| Adjust pH to 4.0 with Phosphoric Acid | | | |
| Total | 100.00% | 100.00% | 100.00% |

Examples 20 and 21 both demonstrated the ability to control both yeast and bacterial residual contamination resulting from the fermentation process.

All patents and literature references cited in this specification are hereby incorporated by reference in their entirety.

Thus, the compounds, systems and methods of the present invention provide many benefits over the prior art. While the above description contains many specificities, these should not be construed as limitations on the scope of the invention, but rather as an exemplification of the preferred embodiments thereof. Many other variations are possible.

Accordingly, the scope of the present invention should be determined not by the embodiments illustrated above, but by the appended claims and their legal equivalents.

What is claimed is:

1. A method for accelerating nutrient uptake in bacteria or yeast without a substantially commensurate increase of biomass, comprising contacting said bacteria or yeast with a mixture of an aerobic yeast fermentation supernatant and a surface-active agent, whereby the nutrient uptake in said bacteria or yeast is increased without a substantially commensurate increase of biomass,
   wherein the mixture of the aerobic yeast fermentation supernatant and the surface-active agent is obtained by:
      fermenting under aerobic conditions a plurality of yeast cells in the presence of a nutrient source,
      heating the plurality of yeast cells after the fermenting step, wherein said heating step comprises increasing the temperature of said plurality of yeast cells to between about 40° to about 60° C. for about 2 to about 24 hours, followed by cooling to less than 25° C.,
      disrupting the cellular structure of some of the plurality of yeast cells to obtain a fermentation product,
      centrifuging the fermentation product to obtain the aerobic fermentation supernatant containing peptides, and
      combining the aerobic fermentation supernatant with the surface-active agent.

2. The method of claim 1, wherein said heating step takes place prior to said disrupting step.

3. The method of claim 1, wherein said disrupting the cellular structure of some of the plurality of yeast cells releases intracellular peptides from the yeast cells into the aerobic fermentation supernatant.

4. The method of claim 1, further comprising substantially separating the plurality of yeast cells from the aerobic fermentation supernatant.

5. The method of claim 4, wherein said separating step takes place prior to said combining step.

6. The method of claim 1, wherein the plurality of yeast cells comprises *saccharomyces cerevisiae*.

7. The method of claim 1, wherein the plurality of yeast cells comprise one or more of *saccharomyces cerevisiae, kluyveromyces marxianus, kluyveromyces lactis, candida utilis, zygosaccharomyces, pichia, or hansanula*.

8. The method of claim 1, wherein the nutrient source comprises a sugar.

9. The method of claim 8, wherein the nutrient source further comprises one or more of diastatic malt, diammonium phosphate, magnesium sulfate, ammonium sulfate zinc sulfate, and ammonia.

10. The method of claim 1, wherein said disrupting the cellular structure of some of the plurality of yeast cells comprises physically disrupting the cellular structure of some of the plurality of yeast cells.

11. The method of claim 10, wherein said physically disrupting comprises subjecting the yeast cells to one or more of a French Press, a ball mill, or a high-pressure homogenizer.

12. The method of claim 1, wherein said disrupting the cellular structure of some of the plurality of yeast cells comprises chemically disrupting the cellular structure of some of the plurality of yeast cells.

13. The method of claim 12, wherein said chemically disrupting comprises combining said plurality of yeast cells with a surface-active agent.

14. The method of claim 12, wherein said chemically disrupting comprises adding about 2.5% to about 10% of a surfactant to a yeast cell suspension and agitating the mixture at a temperature of about 25° C. to about 35° C.

15. The method of claim 12, further comprising physically disrupting a plurality of said yeast cells.

16. The method of claim 1, wherein said surface-active agent comprises a nonionic surfactant.

17. The method of claim 1, wherein said surface-active agent comprises a combination of nonionic and anionic surfactants.

18. The method of claim 1, wherein said surface-active agents comprise ethoxylated linear alcohol or alkyl ether sulfate.

19. The method of claim 1, wherein said bacteria or yeast are mixed in with wastewater.

20. The method of claim 1, wherein said bacteria or yeast are used in a sewage collection system.

21. The method of claim 20, wherein said sewage collection system comprises a cross-flow membrane filtration system.

22. The method of claim 20, wherein said sewage collection system comprises a cooling tower.

23. The method of claim 1, wherein the mixture of the aerobic fermentation supernatant and the surface-active agent is obtained by:
    admixing a plurality of yeast cells with an alcohol at a temperature of at least 40° C. to obtain a peptide product,
    removing the alcohol to obtain the aerobic fermentation supernatant containing peptides, and
    combining the aerobic fermentation supernatant with a surface-active agent.

24. The method of claim 23, further comprising separating the plurality of yeast cells from the aerobic fermentation supernatant.

25. The method of claim 24, wherein said plurality of yeast cells are separated from said aerobic fermentation supernatant by filtration.

26. The method of claim 25, further comprising treating the aerobic fermentation supernatant with charcoal after it is separated from the plurality of yeast cells.

27. The method of claim 23, wherein said alcohol is methanol-denatured alcohol.

28. The method of claim 23, wherein said admixing step comprises admixing a plurality of yeast cells with an alcohol at a temperature of at least 60° C. under agitation for at least about 2 hours.

29. The method of claim 23, further comprising adding water to said aerobic fermentation supernatant.

30. The method of claim 23, further comprising refining the aerobic fermentation supernatant and retaining those peptides having a molecular weight of less than about 30,000 daltons.

31. The method of claim 23, further comprising refining the aerobic fermentation supernatant and retaining those peptides having a molecular weight of less than about 24,000 daltons.

32. The method of claim 23, further comprising refining the aerobic fermentation supernatant and retaining those peptides having a molecular weight of less than about 17,000 daltons.

33. The method of claim 23, further comprising refining the aerobic fermentation supernatant and retaining those peptides having a molecular weight of between about 6,000 daltons and about 17,000 daltons.

34. The method of claim 30, wherein said refining is performed using anion exchange chromatography.

35. The method of claim 30, further comprising refining performed by molecular sieve chromatography.

36. A method for accelerating nutrient uptake in bacteria or yeast without a substantially commensurate increase in biofilm production, comprising contacting said bacteria or yeast with a mixture of an aerobic yeast fermentation supernatant and a surface-active agent, whereby the nutrient uptake in said bacteria or yeast is increased without a substantially commensurate increase of biofilm production,
    wherein the mixture of the aerobic yeast fermentation supernatant and the surface-active agent is obtained by:
        fermenting under aerobic conditions a plurality of yeast cells in the presence of a nutrient source,
        heating the plurality of yeast cells after the fermenting step, wherein said heating step comprises increasing the temperature of said plurality of yeast cells to between about 40° to about 60° C. for about 2 to about 24 hours, followed by cooling to less than 25° C.,
        disrupting the cellular structure of some of the plurality of yeast cells to obtain a fermentation product,
        centrifuging the fermentation product to obtain the aerobic fermentation supernatant containing peptides, and
        combining the aerobic fermentation supernatant with the surface-active agent.

* * * * *